United States Patent [19]

Cahill

[11] Patent Number: 4,771,477

[45] Date of Patent: Sep. 20, 1988

[54] HAT

[75] Inventor: Warren W. Cahill, Lorette, Canada

[73] Assignee: Abe Pauls, Winnipeg, Canada; a part interest

[21] Appl. No.: 54,306

[22] Filed: May 26, 1987

[51] Int. Cl.[4] .................................................. A42B 1/22
[52] U.S. Cl. ............................................ 2/12; 2/197; 2/200
[58] Field of Search ................... 2/12, 200, 177, 175, 2/10, 197

[56] References Cited

U.S. PATENT DOCUMENTS

| 1,624,727 | 4/1927 | Goldberg | 2/197 |
| 1,704,576 | 3/1929 | Pellegrino | 2/197 |
| 3,266,056 | 8/1966 | De Villers et al. | 2/197 X |
| 3,271,778 | 9/1966 | Ferguson | 2/197 X |
| 4,246,659 | 1/1981 | Lyons | 2/200 X |
| 4,335,471 | 6/1982 | Quigley, Jr. et al. | 2/200 X |

FOREIGN PATENT DOCUMENTS

| 2571226 | 4/1986 | France | 2/12 |
| 0096454 | 8/1939 | Sweden | 2/12 |
| 1019163 | 2/1966 | United Kingdom | 2/200 |

Primary Examiner—Peter Nerbun
Attorney, Agent, or Firm—Adrian D. Battison; Stanley G. Ade

[57] ABSTRACT

A hat comprises a flat sheet of flexible but unstretchable self supporting foam of the order of one quarter inch thick. The flat foam sheet is cut to form a forward peak portion and a rearward headband portion with the headband portion having a central opening of a size slightly less than that of the head of the wearer. A plurality of slits extending radially from the hole define a flex portion which can flex upwardly and expand circumferentially to allow the head band to engage around the head of the wearer. More slits are provided at the forward part adjacent the peak to define a concertina type portion which can engage over the forehead of the wearer.

4 Claims, 1 Drawing Sheet 4,771,477

HAT

BACKGROUND OF THE INVENTION

This invention relates to a hat construction of a type which can be manufactured very simply and inexpensively as a "throwaway" novelty item which may be used for example for advertising, promotions and the like.

According to the invention, therefore, there is provided a hat comprising a sheet of flat flexible semi rigid material cut to form a flat closed body having a forward peak portion and a rearward head engaging portion, the head engaging portion having an edge defining a substantially circular closed hole therein inwardly of an outer edge of the head engaging portion and of a size less than that of a head of a person to wear the hat, and a plurality of slits extending generally radially outwardly from the edge of the hole toward said outer edge but terminating at an end thereof at a position spaced from the outer edge such that a band of the hat between said edge and said ends of said slits can flex upwardly and expand circumferentially of the hole to grip the head of the person.

Preferably, there are provided a plurality of further slits each having an inner end spaced outwardly of the hole and an outer end spaced inwardly of the outer edge with each of the further slits arranged intermediate the first series of slits to allow further expansion of the band. In addition there are preferably a yet further series of slits at the forward part of the head engaging portion adjacent the peak portion with each of the yet further slits aligned with a respective one of the first series of slits to allow yet further circumferential expansion of the band portion at that location.

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

DESCRIPTION OF THE DRAWINGS

In the drawings like characters of references indicate corresponding parts in the different figures.

DETAILED DESCRIPTION

Figure 1:
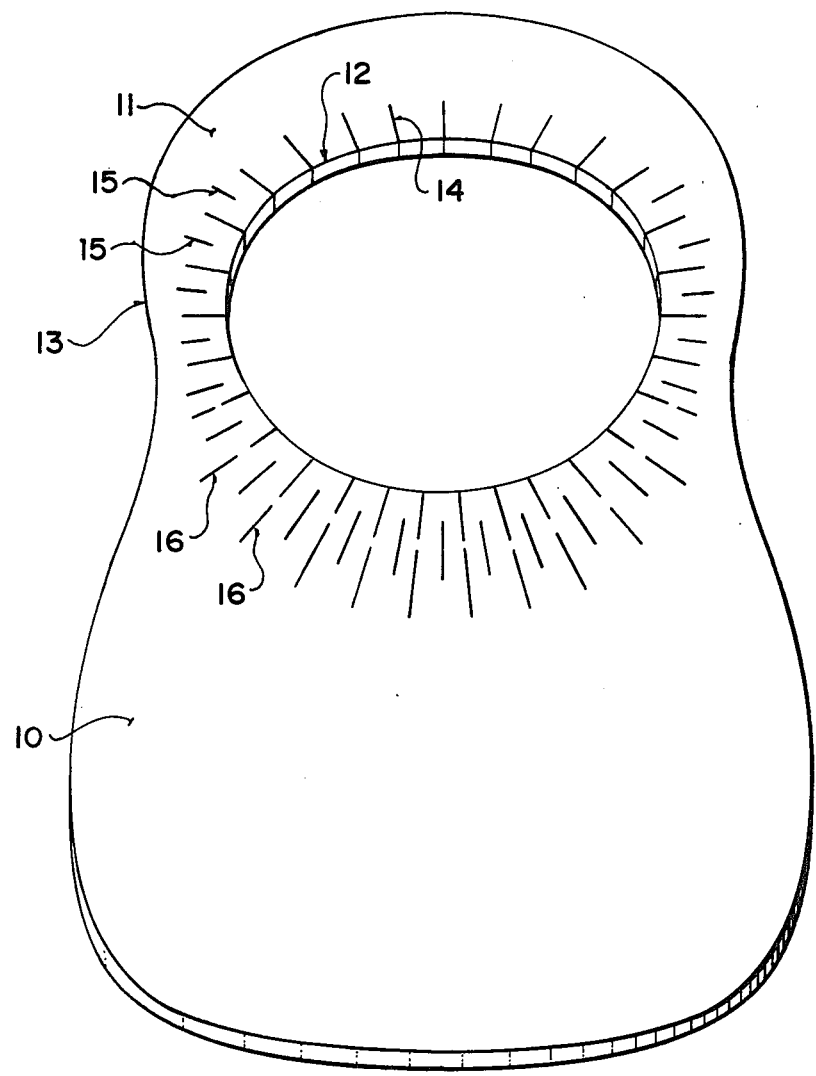
FIG. 1 is an isometric view looking from above of a hat according to the invention.

The hat of the present invention is shown in more detail in the attached figure and comprises a flat sheet of semi rigid foam material which is flexible so as to be deformable out of the flat sheet which is effectively resistant to stretch in the direction of the sheet. Such foams are well known and to provide sufficient strength, a relatively high density foam of sponge of approximately one-fourth inch thickness can be used. Such a foam has sufficient strength to allow the hat and particularly the peak portion to be self supporting that is it does not sag or droop when supported by the head engaging portion rearwardly of the peak portion.

The hat is cut to define a peak area which when in use act as a peak over the eyes of the wearer and a head band portion which will in use extend around the rear of the head of the wearer. The peak portion is indicated at 10 and the head band portion generally indicated at 11.

The peak portion is of conventional shape for a cap type hat with the width slightly greater than the width of the head of the wearer and a forward extent sufficient to provide shading.

The head band portion 11 includes a central substantially circular hole 12 or opening which will pass over the upper part of a wearers head but is of insufficient circumferential extent to normally extend around the wearers head without expansion. The hole is closed and arranged generally centrally of the head band portion and may be slightly deformed from the circular according to a specific design.

A plurality of slots is arranged around the hole with each of the slots or slits extending generally radially from the hole toward the outer edge indicated at 13 of the hat but without reaching the outer edge. A first series of slits 14 are arranged directly around the hole extending in a radial direction with the slits spaced around the circumference of the hole with generally a wider spacing at the rear of the hole that is provided adjacent the front of the hole in the area of the peak portion.

A second series of slots indicated at 15 is also provided with the slots 15 being closed slots that is spaced from both the outer edge of the hat and the outer periphery of the hole so that they terminate wholly within the body of the band portion. The second series of slits is arranged with the slits intermediate two slits of the first series and spaced slightly outwardly therefrom but overlapping therewith. The second series of slits is generally arranged only over the forward area of the hole and preferably around the sides of the hole.

A yet further series of slits indicated at 16 is provided with each slit aligned with one of the slits 14 of the first series and only adjacent the forward part of the hole 12. This allows the forward part of the band defined in the area of the slits to expand in a concertina effect. The length of the slots in the rear areas of the order of three-fourths inch and the total extent of the slits in the forward area is of the order one and a half inches thus defining a band which is wider at the front of the head engaging portion than at the rear. The slits thus allow the material which is otherwise substantially unstretchable to expand in the area of the slits so that the material at this band can thus deform upwardly out of the plane of the hat to wrap around the head of the wearer as a band upstanding from the hat, the width of the band of course being greater at the forward part of the hat to thus cover the forehead of the wearer.

The band is thus automatically adjustable to different head sizes and the tension caused by the opening of the slits and the elastic nature of the material causing it to close those slits provides the tensioning of the band around the head of the wearer to a degree of tension acceptable for comfortable wear and sufficient to retain the hat in place on the wearers head.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A hat consisting solely of a sheet of flat flexible semi-rigid foam material cut to form a flat closed body having a forward peak portion and a rearward head engaging portion, the head engaging portion having an edge defining a substantially circular closed hole therein inwardly of an outer edge of the head engaging portion and of a size less than that of a head of a person to wear the hat, the head engaging portion including an elastically circumferentially expandable band portion at least partly surrounding the hole comprising a first plurality of slits cut in a direction extending generally radially outwardly from the edge of the hole toward said outer edge but terminating at an end thereof at a position spaced from the outer edge, a second plurality of slits each of which is arranged outwardly of and aligned with and radially spaced from a respective one of said first plurality of slits and a third plurality of slits each of which extends generally radially at positions spaced around said hole and each having one end spaced outwardly of the hole and an opposed end spaced from the outer edge with each of said third plurality of slits being arranged intermediate respective adjacent ones of said first plurality of slits and having a radial extent commencing part way along an adjacent one of said first plurality of slits and terminating part way along the respective one of said second plurality of slits, all of said slits being formed substantially without removal of any foam material so that in a relaxed state of the hat sides of the slits lie substantially in contact.

2. The invention according to claim 1 wherein said semi-rigid material is resistant to stretch such that a strip of said head engaging portion exteriorly of said slits remains substantially unstretched when said band is expanded circumferentially.

3. The invention according to claim 1 wherein said material is a dense sponge material having a thickness in the range one-fourth to one-half inch.

4. The invention according to claim 1 wherein said second plurality and third plurality of slits are arranged substantially only at a forward part of said head engaging portion adjacent said peak portion.

* * * * *